US011191931B2

(12) United States Patent
Fojtik (10) Patent No.: US 11,191,931 B2
(45) Date of Patent: Dec. 7, 2021

(54) METHODS FOR MANUALLY INJECTING/ASPIRATING FLUIDS THROUGH SMALL DIAMETER CATHETERS AND NEEDLES AND MANUAL INJECTION/ASPIRATION SYSTEMS INCLUDING SMALL DIAMETER CATHETERS AND NEEDLES

(75) Inventor: Shawn P. Fojtik, Park City, UT (US)

(73) Assignee: PMT PARTNERS, LLC, Park City, UT (US)

( * ) Notice: Subject to any disclaimer, the term of this patent is extended or adjusted under 35 U.S.C. 154(b) by 0 days.

(21) Appl. No.: 12/681,125

(22) PCT Filed: Sep. 30, 2008

(86) PCT No.: PCT/US2008/011305
§ 371 (c)(1),
(2), (4) Date: Apr. 1, 2010

(87) PCT Pub. No.: WO2009/045393
PCT Pub. Date: Apr. 9, 2009

(65) Prior Publication Data
US 2010/0249719 A1    Sep. 30, 2010

Related U.S. Application Data

(63) Continuation-in-part of application No. 11/865,626, filed on Oct. 1, 2007, now abandoned.

(51) Int. Cl.
*A61M 25/10* (2013.01)
*A61B 5/153* (2006.01)
(Continued)

(52) U.S. Cl.
CPC ..... *A61M 25/10182* (2013.11); *A61B 5/1405* (2013.01); *A61B 5/153* (2013.01);
(Continued)

(58) Field of Classification Search
CPC ............ A61M 5/31581; A61M 5/3137; A61M 5/31595; A61M 5/14546; A61M 5/3158;
(Continued)

(56) References Cited

U.S. PATENT DOCUMENTS 530,187 A    12/1894 Lasky
870,573 A    11/1907 Myers
(Continued)

FOREIGN PATENT DOCUMENTS

DE    19647529 A1    5/1998
DE    19732332 A1    2/1999
(Continued)

OTHER PUBLICATIONS

Birnbaum et al. , "Extravasation Detection Accessory: Clinical Evaluation in 500 Patients", Radiology, 1999, pp. 431-438.*
(Continued)

*Primary Examiner* — Lauren P Farrar
(74) *Attorney, Agent, or Firm* — Dentons Durham Jones Pinegar (57) ABSTRACT

A system for increasing rates at which fluids may be manually forced through injection/aspiration elements, such as catheters and needles, includes the injection/aspiration elements, as well as a syringe including a pair of crossed handles, one associated with the barrel of the syringe, the other associated with the plunger of the syringe, to provide a mechanical advantage. The system may include and injection/aspiration element of small (e.g., 0.052 inch or smaller) inner diameter and small outer diameter (e.g., 5 French or less). Such systems enable the use of a single hand to hold and operate a syringe in a variety or procedures, including angiography, angioplasty, discography, glue/cement injection, and a variety of aspiration procedures (e.g., biopsy, sampling, media removal, etc.).

19 Claims, 4 Drawing Sheets

(51) Int. Cl.
  *A61M 5/315* (2006.01)
  *A61M 5/145* (2006.01)
  *A61B 5/15* (2006.01)
  *A61B 5/00* (2006.01)
  *A61F 2/958* (2013.01)
  *A61M 5/00* (2006.01)
  *A61M 5/31* (2006.01)
  *A61B 17/00* (2006.01)

(52) U.S. Cl.
  CPC .... *A61B 5/15003* (2013.01); *A61B 5/150236* (2013.01); *A61B 5/150244* (2013.01); *A61M 5/1452* (2013.01); *A61M 5/315* (2013.01); *A61M 25/104* (2013.01); *A61B 5/4514* (2013.01); *A61B 17/00491* (2013.01); *A61F 2/958* (2013.01); *A61M 5/007* (2013.01); *A61M 5/31581* (2013.01); *A61M 2005/3125* (2013.01); *A61M 2205/3331* (2013.01)

(58) Field of Classification Search
  CPC .. A61M 5/3148; A61M 5/484; A61M 1/0064; A61M 2205/50; A61M 25/10182; A61M 5/315; A61M 5/1452; A61M 25/104; A61M 2205/3331; A61M 5/007; A61M 2005/3125; A61B 5/153; A61B 5/15003; A61B 5/150244; A61B 5/150236; A61B 5/1405; A61B 5/4514; A61B 17/00491; A61F 2/958
  USPC ........ 604/228, 223, 218, 227, 240, 181, 187
  See application file for complete search history.

(56) References Cited

U.S. PATENT DOCUMENTS

| | | |
|---|---|---|
| 901,567 A | 10/1908 | Utschig |
| 1,019,207 A | 3/1912 | Ward |
| 1,218,513 A | 3/1917 | Biron |
| 1,718,596 A | 8/1927 | Smith |
| 2,624,338 A * | 1/1953 | Moore et al. ............... 604/223 |
| 3,016,897 A | 1/1962 | Kendrick |
| 3,598,293 A | 8/1971 | Lee |
| 3,770,169 A | 11/1973 | Roach |
| 4,020,838 A | 5/1977 | Phillips et al. |
| 4,204,539 A | 5/1980 | Van Brugge |
| 4,330,070 A | 5/1982 | Doubleday |
| 4,364,388 A | 12/1982 | Cech |
| 4,382,789 A | 5/1983 | Colombo et al. |
| 4,425,121 A | 1/1984 | Young et al. |
| 4,712,545 A | 12/1987 | Honkanen |
| 4,738,664 A | 4/1988 | Prindle |
| 4,744,789 A | 5/1988 | Johnson |
| 4,808,165 A | 2/1989 | Carr |
| 4,832,692 A | 5/1989 | Box et al. |
| 4,861,339 A | 8/1989 | Jonischkeit |
| 4,923,096 A | 5/1990 | Ennis, III |
| 4,968,303 A | 11/1990 | Clark et al. |
| 4,994,065 A | 2/1991 | Gibbs et al. |
| 5,027,605 A | 7/1991 | Hardesty |
| 5,037,399 A | 8/1991 | Reichert et al. |
| 5,069,421 A | 12/1991 | Kishi et al. |
| 5,078,690 A | 1/1992 | Ryan |
| 5,112,307 A | 5/1992 | Haber et al. |
| 5,133,483 A | 7/1992 | Buckles |
| 5,135,507 A | 8/1992 | Haber et al. |
| 5,139,488 A | 8/1992 | Klein |
| 5,150,488 A | 9/1992 | Yuan et al. |
| 5,176,647 A | 1/1993 | Knoepfler |
| 5,188,610 A | 2/1993 | Rains |
| 5,228,883 A | 7/1993 | Blakely et al. |
| 5,288,285 A | 2/1994 | Carter |
| 5,304,147 A | 4/1994 | Johnson et al. |
| 5,306,147 A | 4/1994 | Dragan et al. |
| 5,306,248 A | 4/1994 | Barrington |
| 5,308,358 A | 5/1994 | Bond et al. |
| 5,336,201 A | 8/1994 | Von der Decken |
| 5,350,365 A | 9/1994 | De Godoy Moreira |
| 5,368,202 A | 11/1994 | Smrt |
| 5,415,630 A * | 5/1995 | Gory et al. ............... 128/898 |
| 5,425,743 A | 6/1995 | Nicholas |
| 5,480,409 A | 1/1996 | Riza |
| 5,499,998 A | 3/1996 | Meade |
| 5,507,727 A | 4/1996 | Crainich |
| 5,507,730 A | 4/1996 | Haber et al. |
| 5,511,556 A | 4/1996 | DeSantis |
| 5,531,708 A | 7/1996 | Woodruff |
| 5,560,373 A | 10/1996 | DeSantis |
| 5,562,655 A | 10/1996 | Mittelstadt et al. |
| 5,591,135 A | 1/1997 | Sullivan |
| 5,591,176 A | 1/1997 | Henderson et al. |
| 5,645,561 A | 7/1997 | Smith et al. |
| 5,722,829 A | 3/1998 | Wilcox et al. |
| 5,733,258 A * | 3/1998 | Lane ............... 604/506 |
| 5,735,874 A | 4/1998 | Measamer et al. |
| 5,749,968 A | 5/1998 | Melanson et al. |
| 5,755,362 A | 5/1998 | Rodriquez, Jr. et al. |
| 5,807,340 A | 9/1998 | Pokras |
| 5,830,194 A | 11/1998 | Anwar et al. |
| 5,851,214 A | 12/1998 | Larsen et al. |
| 5,881,928 A | 3/1999 | Register et al. |
| 5,893,488 A | 4/1999 | Hoag et al. |
| 5,951,517 A | 9/1999 | Lampropoulos et al. |
| 5,961,494 A | 10/1999 | Hogan |
| 5,961,496 A | 10/1999 | Neilsen et al. |
| 5,964,380 A | 10/1999 | Hazzard et al. |
| 5,964,736 A | 10/1999 | Lane |
| 5,992,694 A | 11/1999 | Keller |
| 6,007,515 A | 12/1999 | Epstein et al. |
| 6,047,861 A | 1/2000 | Vidal et al. |
| 6,024,728 A | 2/2000 | Schulz |
| 6,030,368 A | 2/2000 | Anwar et al. |
| 6,080,136 A | 6/2000 | Trull et al. |
| 6,095,814 A | 8/2000 | Petrich et al. |
| 6,117,158 A | 9/2000 | Measamer et al. |
| 6,183,444 B1 | 2/2001 | Glines et al. |
| 6,313,984 B1 | 4/2001 | Lane et al. |
| 6,241,708 B1 | 6/2001 | Reilly et al. |
| 6,264,637 B1 | 7/2001 | Hogan |
| 6,368,307 B1 | 4/2002 | Ziemba et al. |
| 6,406,460 B1 | 6/2002 | Hogan |
| 6,439,439 B1 | 8/2002 | Rickard et al. |
| 6,585,696 B2 | 7/2003 | Peterson et al. |
| 6,607,512 B2 | 8/2003 | Oliver et al. |
| 6,616,634 B2 * | 9/2003 | Benz et al. ............... 604/187 |
| 6,752,781 B2 | 6/2004 | Landau et al. |
| 6,764,466 B1 | 7/2004 | Staats et al. |
| 6,802,824 B2 | 10/2004 | Mickley et al. |
| 7,041,084 B2 * | 5/2006 | Fojtik ............... 604/181 |
| 7,097,636 B2 | 8/2006 | Pessin |
| 7,125,395 B2 | 10/2006 | Hommann et al. |
| 7,717,880 B2 | 5/2010 | Denolly |
| 2002/0022805 A1 | 2/2002 | Lane |
| 2002/0123737 A1* | 9/2002 | Hart ............... A61M 5/007 604/523 |
| 2002/0183698 A1 | 12/2002 | Quinn et al. |
| 2003/0060777 A1 | 3/2003 | Benz et al. |
| 2004/0023850 A1* | 2/2004 | Wolff et al. ............... 514/2 |
| 2004/0116873 A1* | 6/2004 | Fojtik ............... A61M 5/007 604/221 |
| 2004/0116893 A1 | 6/2004 | Spohn et al. |
| 2004/0164097 A1 | 8/2004 | Orecchia et al. |
| 2004/0210200 A1 | 10/2004 | Gerondale et al. |
| 2004/0247453 A1 | 12/2004 | Denolly |
| 2005/0070848 A1* | 3/2005 | Kim et al. ............... 604/140 |
| 2005/0070912 A1 | 3/2005 | Voellmicke |
| 2005/0119754 A1* | 6/2005 | Trieu ............... A61L 31/14 623/17.16 |
| 2005/0137575 A1 | 6/2005 | Thompson et al. |
| 2006/0247578 A1 | 11/2006 | Arguedas et al. |
| 2006/0264966 A1* | 11/2006 | Armstrong ......... A61B 17/8819 606/92 |
| 2006/0270996 A1 | 11/2006 | Fojtik |

(56) References Cited

U.S. PATENT DOCUMENTS

| | | | | |
|---|---|---|---|---|
| 2007/0010788 | A1* | 1/2007 | Evans | 604/97.01 |
| 2007/0265573 | A1 | 1/2007 | Fojtik | |
| 2007/0093760 | A1* | 4/2007 | Wexler | A61M 5/28 604/187 |
| 2008/0027554 | A1* | 1/2008 | Talmadge | A61L 27/50 623/17.16 |
| 2008/0097229 | A1* | 4/2008 | Roy | A61L 27/14 600/500 |
| 2008/0161929 | A1* | 7/2008 | McCormack | A61B 17/7064 623/17.16 |

FOREIGN PATENT DOCUMENTS

| | | |
|---|---|---|
| EP | 0 474 218 | 3/1992 |
| EP | 0 565 045 | 10/1993 |
| EP | 0 919 251 | 6/1999 |
| EP | 1 066 797 | 1/2001 |
| EP | 1 148 834 | 10/2001 |
| EP | 1 301 227 | 4/2003 |
| EP | 1440706 A1 | 7/2004 |
| FR | 2009514 A1 | 2/1970 |
| FR | 2683140 A1 | 5/1993 |
| FR | 2848860 A1 | 6/2004 |
| JP | 59048641 U | 3/1984 |
| JP | 1138370 A | 5/1989 |
| JP | 6296618 A | 10/1994 |
| WO | WO 99/08735 | 2/1999 |
| WO | WO 04/062713 | 7/2004 |

OTHER PUBLICATIONS

Gardiner et al., "Selective Coronary Angiography Using a Power Injector", Am. J. Roentgenole, Apr. 1986, pp. 831-833.

Ganeshkumar et al., "Traditional Versus Automated Injection Contrast System in Diagnostic . . . .", J. Invasive Cardiol., 16(7), 2004, pp. 360-362.

Call et al., "Automated contrast Injection in Contemporary Practice During Cardiac . . . ", J. Invasive Cardiol., 18(10), 2006, pp. 469-471.

Saito et al., "Evaluation of New 4 French Cathertrs by Comparison to 6 French Coronary Artery Images", J. Invasive Cardiol., 11(1), 1999, pp. 13-30.

\* cited by examiner

METHODS FOR MANUALLY INJECTING/ASPIRATING FLUIDS THROUGH SMALL DIAMETER CATHETERS AND NEEDLES AND MANUAL INJECTION/ASPIRATION SYSTEMS INCLUDING SMALL DIAMETER CATHETERS AND NEEDLES

CROSS REFERENCE TO RELATED APPLICATIONS

This application is a national stage application of PCT/US2008/011305, filed Sep. 30, 2008, which claims the benefit of U.S. application Ser. No. 11/865,626, filed Oct. 1, 2007.

FIELD OF THE INVENTION

The present invention relates generally to systems/methods that employ hand-held, manually operated syringes with crossing handles and catheters for introducing fluids into the body of a subject and/or for withdrawing fluids from the body of the subject by squeezing (i.e., bringing together) or opening (i.e., moving apart) the syringe handles and, more specifically, to fluid introduction and/or withdrawal methods that employ catheters having sizes of five French or less.

BACKGROUND

Systems including catheters and syringes are used for a variety of medical procedures in which fluids are introduced or injected into the body of the subject. Examples of these types of medical procedures include a number of angiography, angioplasty, and discography techniques, to name only a few.

Angiography is a procedure by which vessels (e.g., arteries, veins, etc.) or cavities (e.g., heart chambers, etc.) within a subject's body may be visualized. Angiography procedures may be used to evaluate vessels or cavities in a number of locations throughout the body, including coronary blood vessels, cerebral blood vessels, and retinal blood vessels. Angiography typically entails the introduction of a radio contrast agent, which is also commonly referred to as a "contrast agent," "contrast media," "contrast solution," or even more simply as "contrast," into each vessel or cavity that is to be imaged. The use of contrast media is usually necessary since it is often difficult to distinguish between tissues and any openings or cavities defined by the tissues when x-ray and CAT scan technologies are employed. In the cases of blood vessels and heart chambers, blood is also difficult to distinguish from the tissues through which the blood is carried. While the use of contrast media in angiography procedures is widespread, it is also somewhat undesirable due to the fact that it involves the introduction of a foreign substance into the body.

Certain hand-held, hand-actuated syringes have been used in connection with relatively large diameter catheters in angiography, including basic syringes and control syringes. "Basic syringes" as used herein are hand-held, hand-actuated syringes that include a barrel with a flange extending therefrom and that is configured for engagement by a user's fingers. These basic syringes also utilize a plunger having a head that is disposed within the syringe barrel, where the plunger extends beyond the syringe barrel and includes an end that may be configured to be engaged and moved by a user's thumb (e.g., the user's thumb depresses the plunger within the syringe barrel to provide a fluid discharge from the syringe).

Control syringes, which are similar to basic syringes, typically include a pair of loops that extend from opposite sides of the syringe barrel for receiving a user's fingers, along with a loop that extends from an end of the plunger for receiving a user's thumb. Both basic syringes and control syringes have been used to inject contrast through a catheter and to a desired location of a subject's body. Since basic syringes and control syringes are primarily thumb-operated, and since using a single thumb to depress the syringe plunger usually does not provide a great deal of force, catheters with relatively large openings (i.e., catheters having sizes (outer dimensions) of 6 French (F) and larger) are typically used with both basic syringes and control syringes to reduce the amount of resistance on contrast flowing through the catheter and, thus, the amount of force that must be applied by the thumb of the syringe user to cause the contrast to flow through the catheter. Due to variations in thumb positioning relative to the fingers during use since the thumb must move toward the fingers (in injection) or away from the fingers (in aspiration), basic syringes and control syringes typically do not deliver or receive fluids at substantially constant rates over the entire course of moving the plunger along the barrel. Rather, the rate of injection or aspiration decreases significantly before movement of the plunger into or out of the barrel is complete.

Research has shown that when basic syringes and control syringes are used, 6F or larger catheters are required to ensure that contrast is introduced into the blood vessels of a subject at a quick enough rate to ensure dense, uniform opacification of blood vessels with contrast (Gardiner, G A, et al., "Selective Coronary Angiography Using A Power Injector," Am. J. Roentgenol., 146(4):831-33 (1986)), while reducing contrast wastage (Ganeshkumar, A, et al., "Traditional Versus Automated Injection Contrast System in Diagnostic and Percutaneous Coronary Interventional Procedures: Comparison of the Contrast Volume Delivered," J. Invasive Cardiol., 16(7):360-62 (2004)) and contrast-induced nephropathy (i.e., kidney damage) (Call, J, et al., "Automated Contrast Injection in Contemporary Practice during Cardiac Catheterization and PCI: Effects on Contrast-Induced Nephropathy," J. Invasive Cardiol., 18(10):469-71 (2006)). Nonetheless, due to their relatively large size (i.e., 6F and larger), these catheters are known to cause discomfort and arterial complications (Saito, T, et al., "Evaluation of New 4 French Catheters by Comparison to 6 French Coronary Artery Images," J. Invasive Cardiol., 11(1):13-30 (1999) (hereinafter "Saito").

Despite the advantages of smaller (less than 6 F) catheters, their small lumens increase resistance to flow, diminishing the rates at which contrast may be introduced to a desired location to unacceptably low levels when using basic syringes and control syringes. Consequently, power injectors have been utilized to deliver contrast with catheters that are smaller than 6F.

Angioplasty (or percutaneous transluminal angioplasty (PTA)) is a technique by which the lumens through blood vessels are mechanically widened. When the manipulated blood vessels are associated with the heart, the procedure is referred to as "coronary angioplasty." "Peripheral angioplasty" includes angioplasty procedures that are affected on non-coronary blood vessels, such as renal arteries, the carotid arteries, and blood vessels in legs. Angioplasty procedures require catheters that often include angioplasty balloons at or near the distal ends thereof. Angioplasty balloons inflate, or expand or dilate, and deflate under control of a so-called "angioplasty inflator" (e.g., by introducing air or other gases into the catheter). Sometimes, the catheters and/or angioplasty balloons are used to position stents, which hold blood vessels open, at desired locations within the blood vessels. Catheter-introduced drug therapies may also be performed in connection with angioplasty.

The angioplasty inflators that are typically used during angioplasty processes are relatively complex syringes that include pressure gauges and plunger locks. As they are often used in connection with angioplasty balloons, angioplasty inflators are typically configured to deliver the relatively high pressures that are required to inflate the angioplasty balloons. Use of an angioplasty inflator requires at least two hands for simple tasks such as locking the plunger in place relative to the barrel, as well as for microadjustment of the location of the plunger along the length of the barrel. Thus, when these tasks are performed, a single user cannot hold the catheter in place to prevent its ejection from the body of a subject as pressurized fluid or gas is introduced into the catheter.

In discography, saline, contrast media, or a combination thereof is introduced into an intervertebral disk, which is located between two vertebrae of the spinal column of a subject. Typically, the skin and muscle of the subject is pierced by a first, guide needle, which is inserted until it reaches the outer surface of the disk. A smaller, second needle, is then inserted into the first needle, and into the disk, near its center. Contrast media is then (typically manually) injected into the disk through the second needle. Leakage of the contrast media from the center of the disk, which may be visualized by x-ray or CAT scan, is indicative of damage that may be the cause of back pain. To facilitate the manual injection of contrast media into a disk at a suitable rate, the contrast-injection needles that are used are relatively large (e.g., about 16 gauge (i.e., with an outer diameter of about 1/16 inch (about 1.59 mm) and an inner diameter of about 0.047 inch (about 1.2 mm)). Even larger guide needles (typically about 13 gauge (i.e., having an outer diameter of about 1/13 inch (about 1.95 mm)) and an inner diameter of about 0.071 inch (about 1.8 mm) or larger than 13 gauge) are needed to accommodate such large contrast-injection needles. As a consequence of the use of large needles, subjects that undergo discography usually experience significant post-procedure pain. Sometimes, tissue damage, including damage to an evaluated disk, may also occur. Due to these undesirable aspects of discography, it is a procedure that is typically reserved for subjects that suffer from chronic back pain, and is not even used by some spine care physicians.

Syringes, including both manually operated and power injector syringes, of ever-increasing complexity have been developed to facilitate the introduction and/or withdrawal of fluids at high pressure. Unfortunately, the mechanisms that are intended to enable fluid introduction at high pressures or rates may adversely impact the tactile feedback that is often highly valued by physicians since it allows them to instinctively and immediately respond to complications or other unforeseen events that might occur during a particular procedure. Furthermore, these complex devices, particularly power syringes, are very costly to use, in terms of both money and time.

SUMMARY

The present invention includes systems/methods for introducing fluids into and/or withdrawing fluids from the body of a subject. Such a system/method includes use of a hand-held, manually operated syringe with crossing handles that are configured to be engaged/manipulated by a single hand of a user, along with a catheter that has a size of about five French or less (e.g., an outer diameter of no more than about 1.67 mm), or another "small inner diameter element," such as a needle, with an inner diameter that is the same as or less than that of a five French catheter. In one embodiment, a four French catheter is used (e.g., an outer diameter of no more than about 1.35 mm). For at least certain applications, the length of the catheter may be at least about 65 cm.

In one embodiment of the above-noted system/method, fluids are introduced into the body or withdrawn from the body through a small inner diameter element (e.g., a five French catheter or smaller) at a rate of about 0.5 mL or more, 1.0 mL or more, 2.0 mL or more, 3 mL or more, even 5 mL or more, per second. By enabling the use of smaller elements (e.g., catheters, needles, etc.) in invasive processes, systems that incorporate teachings of the present invention facilitate access to sites that were not previously accessible in systems that included manually-operated syringes where larger catheters or needles were required to provide desired delivery or aspiration rates, reduce the potential for procedure-related complications, reduce discomfort to subjects, and/or allow subjects to heal faster once a procedure is complete. In another embodiment, fluids are introduced into the body or withdrawn from the body through a catheter, needle, or the like at a pressure and rate that exceeds that available with conventional hand-held syringes. In still another embodiment, a hand-held manually-operated syringe with crossing handles (that are configured to be engaged/manipulated by a single hand of a user) may be used to cause fluids to move through a catheter with a lumen that is partially occupied by another element, such as a wire or the like.

Another aspect of the present invention includes systems for introducing and/or aspirating fluids from the body of a subject. An embodiment of such a system includes a hand-held, manually operated syringe with handles that are configured to be engaged/manipulated by a single hand of a user, and furthermore that are arranged to provide a user with a mechanical advantage without eliminating tactile feedback, along with a catheter with a size of about five French or less.

Other features and advantages of the present invention will become apparent to those of ordinary skill in the art through consideration of the ensuing description, the accompanying drawings, and the appended claims.

DETAILED DESCRIPTION

Figure 1:
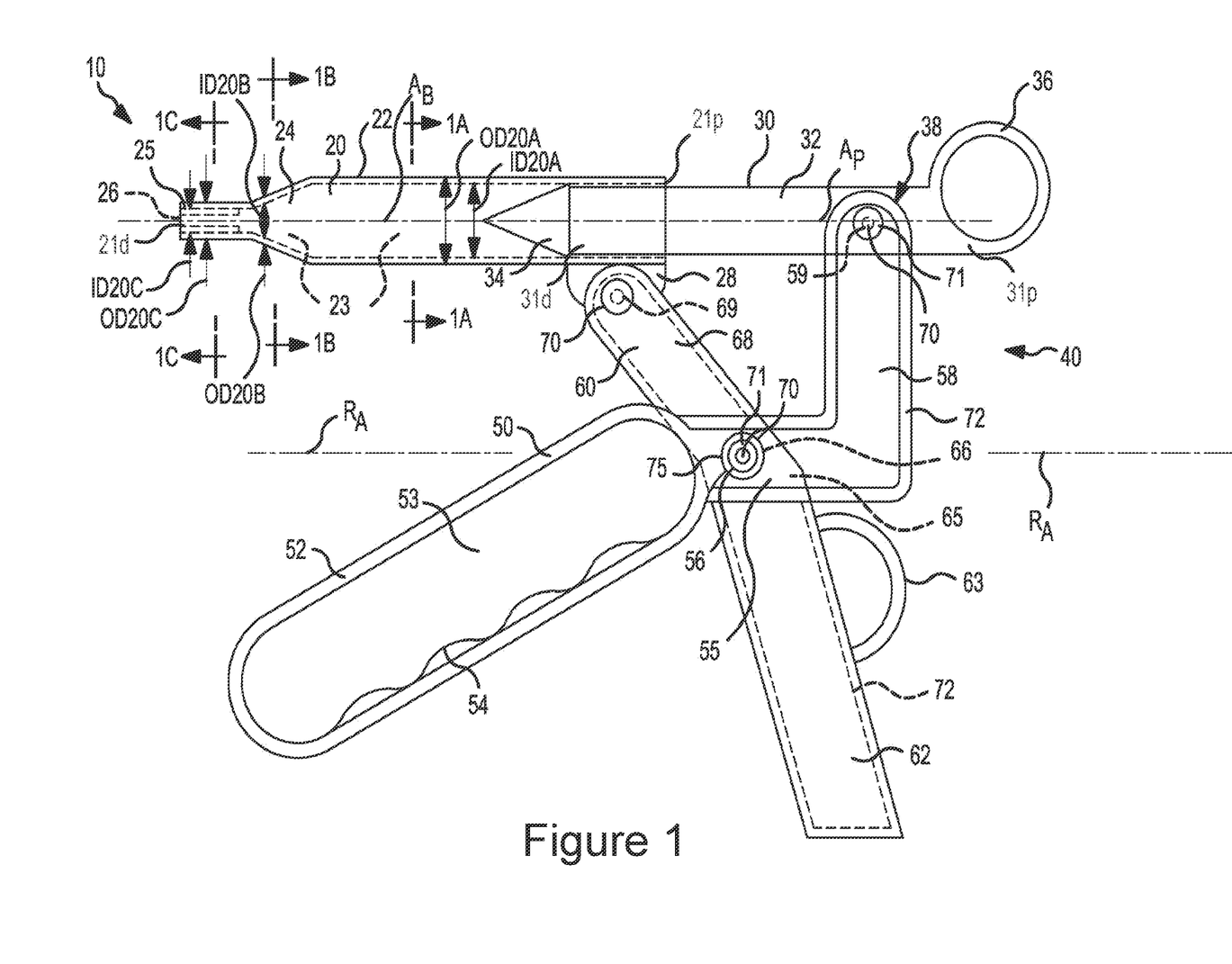
FIG. 1 is a side view of a hand-held, manually operated syringe, including a syringe barrel, a plunger that is longitudinally movable within a receptacle of the syringe barrel, and a scissor-grip handle that includes two members with three pivotal connection points, a first between a first member of the handle and the syringe barrel, a second between the second member of the handle and the plunger, and a third between the two handle members.

FIG. 1 illustrates an exemplary embodiment of a hand-held, hand-actuated or manually operated syringe 10 (hereafter "power syringe 10"). Generally, the power syringe 10 is configured to be held by a user with a single hand, and further is configured to be actuated by this same single hand. For instance, forces that are used to discharge fluid from the power syringe 10 are provided by a scissor-grip handle 40 of the power syringe 10 being engaged/manipulated by a single hand of a user.

Power syringe 10 includes a barrel 20, a plunger 30 associated with barrel 20, and a scissor-grip handle 40 which causes plunger 30 to move longitudinally relative to barrel 20. One or both of barrel 20 and plunger 30 may be removable from handle 40 to facilitate the replacement of these elements and the reuse of handle 40.

Barrel 20 of power syringe 10 is an elongate member with a hollow interior extending through the length thereof. Along the majority of its length, barrel 20 is substantially uniform in both cross-sectional shape and cross-sectional dimensions. The region of barrel 20 having such substantial cross-sectional uniformity is referred to herein as body 22. As depicted, body 22 extends from a proximal end 21p of barrel 20 to a tapered section or region 24 thereof. A syringe tip 25 is located on the opposite side of tapered section 24, at the distal end 21d of barrel 20.

As shown in FIGS. 1 and 1A-1C, the distances across opposed points of various cross-sections taken transverse to longitudinal axis $A_B$ of barrel 20 on the outer surface of barrel 20 or the outer diameter of barrel 20 are collectively referred to herein as OD20. The corresponding distances across opposed points of various cross-sections taken transverse to longitudinal axis $A_B$ on the inner surface of barrel 20 or the inner diameter of barrel 20 are collectively referred to herein as ID20.

Figure 1A:
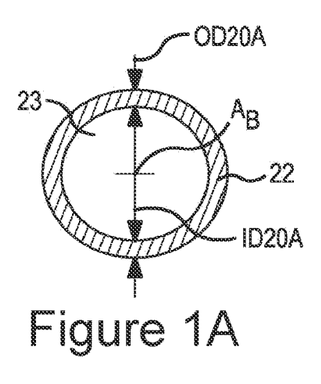
FIGS. 1A-1C are cross-sections taken along lines 1A-1A, 1B-1B, and 1C-1C, respectively, of FIG. 1.
Figure 1B:
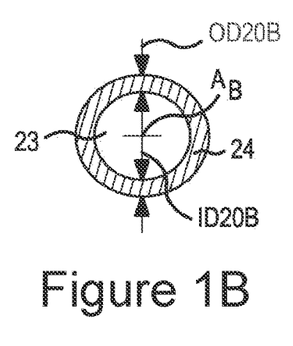
Figure 1C:
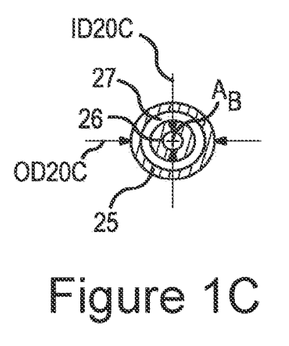

As is depicted in FIGS. 1 and 1A, both OD20A and ID20A remain substantially the same along the substantial length of a body 22 of barrel 20. At tapered region 24, OD20 and ID20, which are respectively depicted at one location along the length of tapered region 24 as OD20B and ID20B, gradually (either linearly or along a curve) decrease from the sizes of OD20A and ID20A of body 22 to the much smaller sizes OD20C and ID20C of syringe tip 25. At syringe tip 25, the sizes of OD20C and ID20C are again substantially constant. It is preferred that the taper of tapered region 24 occur at an angle of about 15° to longitudinal axis $A_B$ of barrel 20, although other taper angles may be utilized.

Figure 2:
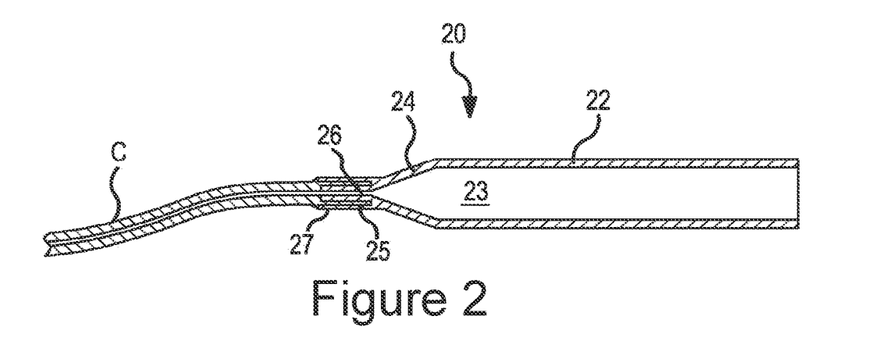
FIG. 2 is a cross-sectional representation of the syringe barrel of the syringe of FIG. 1, illustrating the syringe barrel in an assembled relationship with a catheter.

Turning now to FIG. 2, within body 22 and tapered region 24 of barrel 20, the hollow interior thereof forms a receptacle 23. The volume of receptacle 23 is preferably suitable for the desired use of power syringe 10. For example, in applications where only small volumes of materials will be injected with power syringe 10, barrel 20 may include a receptacle 23 with a relatively small volume (e.g., 5 cubic centimeters ("cc"), 7.5 cc, 10 cc, 12.5 cc etc.). When power syringe 10 is to be used to inject larger volumes of materials, the volume of receptacle 23 may also be larger (e.g., 20 cc, 30 cc, 60 cc, etc.). Alternatively, receptacle 23 of barrel 20 may have other standard syringe volumes or a volume that is tailored to a specific use for power syringe 10.

The power syringe 10 is shown being interconnected with a catheter C in FIG. 2. The hollow interior of syringe tip 25 is referred to herein as a lumen 26. Lumen 26 may have a diameter of as small as about 1 mm (0.40 inch) or smaller. Of course, syringe tips 25 with different sizes of lumens 26 may be utilized, as the size of a lumen 26 depends at least partially upon the gauge of a needle or the lumen size of a catheter to be coupled with syringe tip 25. In one embodiment, the catheter C is less than 6 French (e.g., an outer diameter less than 2 mm). In one embodiment, the catheter C is a 5 French (e.g., an outer diameter of about 1.67 mm) or smaller catheter. Another embodiment has the catheter C being a 4 French catheter (e.g., an outer diameter of about 1.35 mm). At least certain applications may require that the catheter C be at least about 65 cm in length.

In addition, in order to facilitate the coupling of a needle or catheter with syringe tip 25, syringe tip 25 includes a coupling member 27 at or near the distal end 21d of barrel 20. Although FIG. 2 depicts coupling member 27 as including a cylindrically shaped recess that extends partially into syringe tip 25, coupling members of other configurations, including, without limitation, threaded or non-threaded coupling members that facilitate the coupling of a needle, catheter, or other member to an outer surface of syringe tip 25, may also be utilized.

Referring back to FIG. 1, barrel 20 also includes a handle connection element 28. As depicted, handle connection element 28 extends from body 22 at proximal end 21p of barrel 20 and includes an aperture formed therethrough. The aperture is sized and configured to receive a hinge element 70 and, thus, to facilitate the connection of a member of handle 40 to barrel 20.

While FIG. 1 depicts barrel 20, receptacle 23, and lumen 26 as having substantially cylindrical shapes with circular cross-sections taken transverse to a longitudinal axis $A_B$ of barrel 20, syringe barrels with any other suitable cross-sectional shapes (e.g., ovals, ellipses, polygons, etc.) may also be utilized.

Plunger 30 is an elongate member with dimensions that permit plunger 30 to be inserted into receptacle 23 of barrel 20 through proximal end 21p thereof. Plunger 30 includes a body 32 and a head 34 at the distal end 31d of body 32. The proximal end 31p of body 32 and, thus, of plunger 30 is configured to have force applied thereto to facilitate movement of plunger 30 in both directions along a longitudinal axis $A_P$ of plunger 30.

Head 34 of plunger 30 preferably comprises a somewhat deformable, resilient member. By way of example, head 34 may be formed from silicone or any other resilient polymer (i.e., rubber) that is suitable for use in medical applications. The shape of head 34 is preferably substantially complementary to a shape of the portion of receptacle 23 of barrel 20 that is located within tapered region 24 and a portion of body 22 adjacent thereto. The size of head 34 is preferably substantially the same as or somewhat larger than the correspondingly shaped portion of receptacle 23 so as to facilitate the substantial displacement of fluid from receptacle 23 as plunger 30 is fully inserted therein.

Preferably, in order to facilitate movement of head 34 of plunger 30 along the full length of receptacle 23, the length of plunger 30 is greater than the combined lengths of body 22 and tapered region 24 of barrel 20. Of course, in order to apply the amount of force necessary to move plunger 30 through the length of receptacle 23, body 32 of plunger 30 is preferably formed from a more rigid material than that of head 34. Accordingly, head 34 preferably includes a receptacle (not shown) that is configured to receive a corresponding head connection protrusion (not shown) at the distal end of body 32, as known in the art.

Proximal end 31p of plunger 30 includes a handle connection element 38. Handle connection element 38 includes an aperture formed through body 32 of plunger 30 at a location that facilitates the pivotal connection of a member of handle 40 thereto by way of a hinge element 70. In addition, proximal end 31p of plunger 30 may include a secondary movement element 36, such as a loop or another member by which an individual may cause plunger 30 to move in one or both directions along longitudinal axis $A_P$ thereof.

Handle 40 includes two elongate members, a first member or lever 50 and a second member or lever 60. First member 50 and second member 60 are pivotally connected with one another in a manner that, along with the shapes of first and second members 50 and 60, provides leverage so as to decrease the amount of force that must be exerted by an individual's hand to move plunger 30 relative to barrel 20.

First member 50, which is configured to be held with an individual's fingers, includes a gripping end 52 and a plunger attachment end 58. In addition, first member 50 includes pivotal connection element 56 positioned at a central region 55 thereof, which is located substantially centrally along the length thereof, to facilitate connection of first member 50 to second member 60 of handle 40. Pivotal connection element 56 includes an aperture that has a circular shape and that receives a hinge element 70, or pivot pin, which, in turn, connects first member 50 and second member 60 to one another.

As shown, first member 50 includes an elongated loop 53 along gripping end 52, through which an individual's fingers may be inserted. Alternatively, or in addition to loop 53, gripping end 52 may include a finger grip 54 that is contoured so as to comfortably receive the fingers of an individual.

Plunger attachment end 58 includes (e.g., terminates at) a plunger connection element 59 that facilitates the pivotal connection of first member 50 to the corresponding handle connection element 38 of plunger 30. Plunger connection element 59 may comprise an aperture that is configured to receive hinge element 70. First member 50 and plunger 30 are pivotally connected to one another by positioning plunger attachment end 58 against the appropriate location of plunger 30 with plunger connection element 59 and an aperture (not shown) of handle connection element 38 in alignment. A single hinge element 70 is then inserted through both plunger connection element 59 and the noted aperture of handle connection element 38. Hinge element 70 preferably includes an enlarged head 71 at each end thereof to maintain the assembled, pivotal relationship of plunger 30 and first member 50. Of course, other known types of pivotal connection arrangements between plunger 30 and first member 50 and their corresponding elements may be utilized.

First member 50 is bent, or angled, at some point along the length thereof, between gripping end 52 and plunger attachment end 58, to at least partially provide the desired amount of leverage for forcing plunger 30 to move longitudinally through receptacle 23 of barrel 20. As shown in FIG. 1, first member 50 is angled at two locations, a first of which is located between gripping end 52 and central region 55 and a second of which is located between central region 55 and plunger attachment end 58. Although FIG. 1 depicts gripping end 52 and central region 55 as being oriented at an angle of about 140° relative to one another and central region 55 and plunger attachment end 58 as being oriented at an angle of about 90° relative to one another, other angles and bend locations may be utilized.

Second member 60 of handle 40 is an elongate member that is configured to be held by an individual's palm or thumb. Second member 60 includes a gripping end 62 and a barrel attachment end 68, as well as a central region 65 located between gripping end 62 and barrel attachment end 68. Gripping end 62 of second member 60 may include a thumb loop 63 through which the thumb of an individual using power syringe 10 may be inserted.

Central region 65 of second member 60 includes a pivotal connection element 66 that corresponds to pivotal connection element 56 of first member 50. Pivotal connection element 66 may comprise an aperture formed through central region 65 and configured to receive hinge element 70. Upon properly orienting first member 50 and second member 60 relative to one another in an assembled relationship thereof and aligning the aperture of first member 50 with the aperture of second member 60, hinge element 70 may be inserted through the apertures to pivotally connect first and second members 50 and 60 to one another. Hinge element 70 preferably includes an enlarged head 71 at each end thereof to maintain the assembled, pivotal relationship of first member 50 and second member 60.

Handle 40 may additionally include a resilient element (e.g., a spring), which may be associated with first and second members 50 and 60 (e.g., at or near hinge element 70) in such a way as to force first and second members 50 and 60 apart from one another when they are not being held together.

When first and second members 50 and 60, or variations thereof, have been properly assembled with one another, it is preferred that practically any adult user be able to properly position their fingers on gripping end 52 and their thumb or palm against gripping end 62 while gripping ends 52 and 62 are spaced a maximum distance apart from one another with head 34 of plunger located at proximal end 21p of barrel 20. Therefore, a single hand of a user may simultaneously engage and manipulate the members 50, 60.

Barrel attachment end 68 includes (e.g., terminates at) a barrel connection element 69 that facilitates the pivotal connection of second member 60 to the corresponding handle connection element 28 of barrel 20. As depicted, barrel connection element 69 comprises an aperture that is configured to receive a hinge element 70. Second member 60 and barrel 20 are pivotally connected to one another by properly positioning barrel attachment end 68 and handle connection element 28 against one another, with the apertures thereof in alignment, and inserting a single hinge element 70 through both barrel connection element 69 and handle connection element 28. Hinge element 70 preferably includes an enlarged head 71 at each end thereof to maintain the assembled, pivotal relationship of barrel 20 and second member 60. Of course, other known types of pivotal connection arrangements between barrel 20 and second member 60 and their corresponding elements may be utilized.

Second member 60 of handle 40 may be bent, or angled, to increase the leverage provided by first member 50 and the scissor-like arrangement of first member 50 and second member 60. As illustrated, second member 60 is bent at central region 65 thereof to position gripping end 62 in proximity to gripping end 52 of first member 50 when first member 50 and second member 60 are in an appropriate assembled relationship. With further regard to the noted scissor-like arrangement between the first member 50 and second member 60, the side view of FIG. 1 shows a reference axis $R_A$ that extends through the hinge element 70 (that pivotally interconnects the first member 50 and the second member 60) and that is parallel to both the longitudinal axis $A_B$ of barrel 20 and the longitudinal axis $A_p$ of plunger 30. Note that both plunger attachment end 58 (of first member 50) and barrel attachment end 68 (of second member 60) each extend relative to the hinge element 70 (between first member 50 and second member 60) onto one side of this reference axis $R_A$ (on the side that is "above" the reference axis $R_A$ in the side view of FIG. 1), and that both gripping end 52 (of first member 50) and gripping end 62 (of second member 60) each extend relative to the hinge element 70 (between first member 50 and second member 60) onto the opposite side of this reference axis $R_A$ (on the side that is "below" the reference axis $R_A$ in the side view of FIG. 1).

Of course, one or both of first member 50 and second member 60 may include reinforcement ribs 72 or other reinforcement structures along at least a portion of the length thereof. As depicted, reinforcement ribs 72 are positioned along the edges of first member 50 and second member 60. Reinforcement ribs 72 may be positioned to prevent side-to-side bending of first member 50 or second member 60 during use of handle 40 to move plunger 30 relative to barrel 20.

While the various elements of power syringe 10 may be manufactured from any suitable material or materials, it is preferred that each of the elements of the power syringe 10 be formed by injection molding processes so as to afford low manufacturing cost and, consequently, to facilitate single-use, or disposability, of the power syringe 10. For the more rigid elements, which, in power syringe 10 (FIG. 1) include substantially all of the elements thereof with the exception of head 34 of plunger 30, polycarbonates, such as LEXAN®, manufactured by General Electric, or MAKROLON®, manufactured by Miles Chemicals, may be used. Of course, other medical grade plastics having properties (strength, rigidity, structural integrity, ability to be adequately sterilized while maintaining other desired properties, etc.) that are suitable for the desired functions of the various elements of a power syringe may be used to form those elements. Alternatively, suitable metals, such as stainless steel, which have the desired properties, may be used to form one or more of the elements of a power syringe 10.

The three-pivot-point configuration of handle 40 provides sufficient leverage that the force applied by a single hand of a user will be translated into an adequate amount of force upon plunger 30 and within receptacle 23 to force even relatively high viscosity fluids into and out of receptacle 23. Moreover, the configurations of members 50 and 60 of handle 40 facilitate gripping thereof with a single hand, the fine motor skills of which can be used in such a way as to precisely control the amount of fluid being introduced into or discharged from receptacle 23 of syringe barrel 20.

The power syringe 10 may be used in a variety of different procedures, including, without limitation, injecting medicines or drugs into an individual, either through a hypodermic needle into the individual's tissues or intravenously (i.e., into a vein of an individual), introducing dyes or other indicator solutions into the bloodstream of a particular location of individual's body (e.g., in angiography), introducing a gas, air, or another gas mixture into an angioplasty balloon to inflate the same in a process which is typically referred to as percutaneous transluminal coronary angioplasty ("PTCA"), or obtaining samples of blood, other fluids, or tissues (e.g., with a biopsy needle or other biopsy instrument). The power syringe 10 may also be used to remove air or gas from such a balloon or to obtain samples from the body of an individual, as well as in other applications where syringes have been used.

Figure 3A:
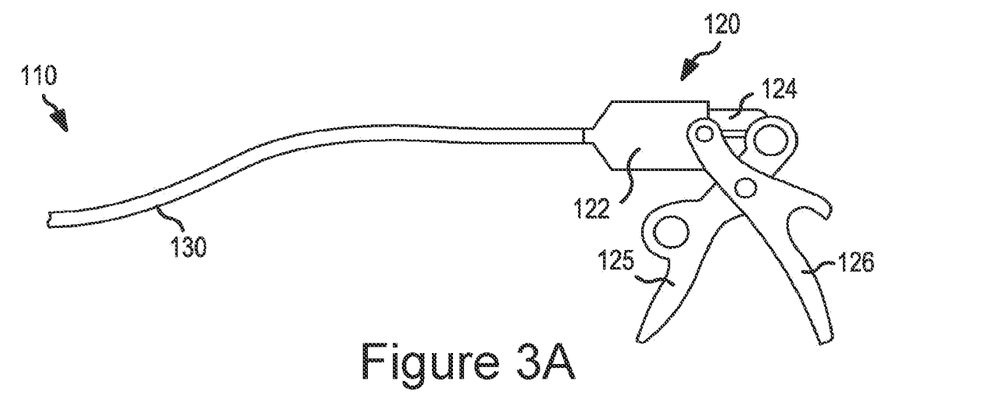
FIG. 3A is a schematic representation of a system that includes a hand-held, hand-operated syringe and a catheter having a size of less about five French or less and configured, for example, for use in angiography processes.

Another embodiment of a system for injecting and/or aspirating fluids from the body of a subject is illustrated in FIG. 3A and is identified by reference numeral 110. Specifically, system 110 includes a syringe 120 and an injection/aspiration element 130 (e.g., a catheter 130). The syringe 120 utilizes the actuation fundamentals discussed above in relation to the power syringe 10 of FIG. 1. In one embodiment, the catheter 130 is a 5 French (e.g., an outer diameter of about 1.67 mm) or smaller catheter. Another embodiment has the catheter 130 being a 4 French catheter (e.g., an outer diameter of about 1.35 mm). At least certain applications may require that the catheter 130 be at least about 65 cm in length.

Syringe 120 is a hand-held, manually operated syringe. As used herein, the term "hand-held," when used with the term "syringe," includes syringes that are configured to be held within one hand of a user (e.g., a physician or other healthcare provider). The phrases "hand-actuated," "manually operated," or the like, when used in conjunction with the term "syringe," indicates that the syringe may be hand operated and, when used in tandem with "hand-held" and "syringe," signifies that the syringe may be held and operated with the same (i.e., one) hand.

In addition to being hand-held and manually operable, syringe 120 provides its user with both a mechanical advantage and tactile feedback. Non-limiting examples of such a syringe include those described in U.S. Pat. No. 7,041,084, in U.S. Patent Application Publication US-2006-0270996-A1, in U.S. patent application Ser. No. 11/431,420, and in U.S. Provisional Patent Application Ser. Nos. 60/853,817 and 60/853,878, the entire disclosure of each of which is hereby incorporated herein by this reference.

Syringe 120 includes a barrel 122, a plunger 124, and a pair of handles 125 and 126 associated with barrel 122 and plunger 124. The syringe 120 may be configured for injection (e.g., FIG. 3B) or for aspiration (e.g., FIG. 3C). In the embodiment of syringe 120 depicted in FIG. 3B, which is an injection configuration, a coupling end 125c of one handle 125 is associated with (e.g., coupled to) a proximal end 124p (relative to a user of syringe 120) of plunger 124, while a coupling end 126c of the other handle 126 is associated with (e.g., coupled to) a proximal end 122p of barrel 122. Handles 125 and 126 are joined at a pivot point 127. When grasping, or bottom, ends 125g and 126g of handles 125 and 126 are forced toward one another (e.g., squeezed together), handles 125 and 126 pivot about pivot point 127 and plunger 124 is forced distally into barrel 122.

Figure 3B:
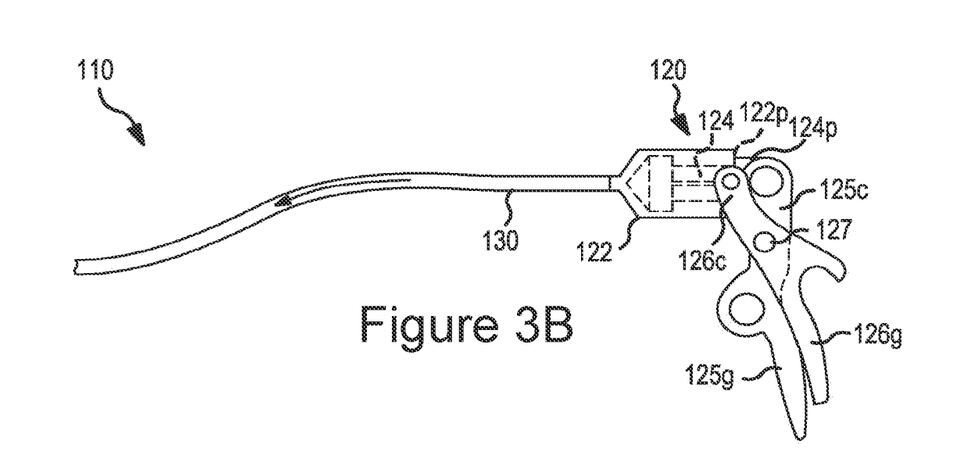
FIG. 3B schematically shows the syringe from the system of FIG. 3A in an injection configuration.
Figure 3C:
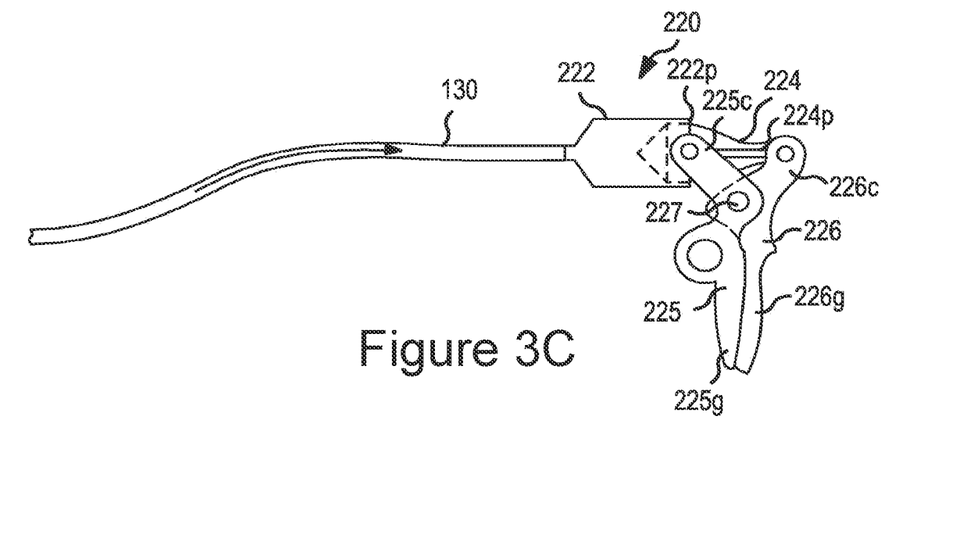
FIG. 3C schematically shows the syringe from the system of FIG. 3A in an aspiration configuration.

In an aspiration shown in FIG. 3C (an adaptation of the syringe 120 of FIGS. 3A and 3B), syringe 220 includes a handle 225 that is bent to resemble a "V." The point of the "V" of handle 225 crosses, or overlaps, handle 226 at a pivot point 227 where handles 225 and 226 are coupled to each other. A coupling end 225c of handle 225 is associated with a proximal end 222p of barrel 222, while a coupling end 226c of handle 226 is associated with a proximal end 224p of plunger 224. Thus, when grasping, or bottom, ends 225g and 226g of handles 225 and 226 are forced (e.g., squeezed) together, plunger 224 is drawn proximally out of barrel 220.

With continued reference to both FIG. 3B and FIG. 3C, handles 125 and 126 and handles 225 and 226 are pivotally coupled (e.g., by a hinge) to one another at respective pivot points 127, 227. The length of the portion (i.e., coupling end 125c, 126c, 225c, 226c) of each handle 125, 126, 225, 226 between pivot point 127, 227 and plunger 124, 224, or barrel 122, 222 is shorter than the length of the portion (i.e., grasping end 125g, 126g, 225g, 226g) of each handle 125, 126, 225, 226 located beneath pivot point 127, 227 (i.e., on the opposite side of pivot point 127, 227 from barrel 122, 222 and plunger 124, 224) and that are to be gripped by a user's hand. Such an arrangement, which resembles pliers, provides a user of syringe 120, 220 with a mechanical and ergonomic advantage. In addition, handle 125, 225 may be shorter than handle 126, 226, which may provide further mechanical advantage. The mechanical advantage provided by the crossing pivotal arrangement of handles 125 and 126 and handles 225 and 226, as well as by their relative lengths, has recently been found to be useful for quickly forcing fluid through (injection or aspiration) a small inner diameter injection/aspiration element 130 that has been coupled to barrel 122, 222. It has also been discovered that the arrangement of handles 125 and 126 and handles 225 and 226 enables a user to maintain a constant rate of injection or aspiration over the entire course of travel of plunger 124, 224 through barrel 122, 222.

In different implementations, syringes 120, 220 with barrels 122, 222 of different volumes may be used. Without limitation, syringe 120, 220 may include a barrel having a volume of 7.5 ml, 10 ml, 12.5 ml, 25 ml, 50 ml, etc. In some embodiments, handles 125 and 126 and handles 225 and 226 may be configured to be reused with different single-use cartridges that include syringe barrels 122, 222, plungers 124, 224, and plunger tips, which may be configured for quick assembly with and disassembly from handles 125 and 126 and handles 225 and 226.

One specific embodiment of injection/aspiration element 130 is a catheter. A catheter 130 that may be used in system 110 may have a length of at least about 65 cm. Catheter 130 may have an outer dimension (e.g., outer diameter, etc.), or size, of about five French (e.g., 1⅔ mm) or less (e.g., four French (1⅔ mm), three French (1 mm), etc.). An inner dimension (e.g., inner diameter) of such a catheter may be about 0.047 inch (about 1.2 mm) or smaller. Alternatively, injection/aspiration element 130 may be a dilation catheter.

System 110 may be used in a variety of procedures, including, but not limited to, angiography and angioplasty procedures. Of course, the specific features of syringe 120 (e.g., injection, aspiration, extent of mechanical advantage, etc.) and catheter 130 (e.g., configured for use with contrast media, balloon, etc.) depend upon the procedure in which system 110 is to be used, as well as the acts that are to be performed by way of the procedure.

The syringes 10, 120 may be used to deliver contrast for angiography procedures by way of single-hand (manual) operation in conjunction with 5F and 4F catheters. Angiography in this manner should minimize discomfort to the subject on whom (which) the procedure is being formed, while delivering contrast at a sufficient rate to optimize the density of contrast-enhanced images, to minimize wastage of contrast, and to minimize the potential for nephropathy.

In one embodiment of the present invention, fluids are introduced into the body or withdrawn from the body through a small inner diameter element (e.g., a five French catheter or smaller) at a rate of about 0.5 mL or more, 1.0 mL or more, 2.0 mL or more, 3 mL or more, even 5 mL or more, per second.

Tables 1-6 present data on various combinations of a control syringe, a syringe in accordance with syringes 10 and 120 addressed herein, various catheters, and various types of contrast media, while Tables 7-8 provides data for where the liquid is water versus contrast media. The parenthetical "mL" designation that accompanies the syringe designation identifies the size of the syringe in each of Tables 1-8. The average flow rate (in mL/sec) that was realized by each of three different users is presented for each of the various combinations in each of Tables 1-8. The average flow rate that is presented in each of Tables 1-8 for each user and syringe/catheter combination was derived from five separate syringe discharges. Each syringe discharge was directed into an appropriate container (e.g., a graduated cylinder), and the users were instructed to discharge the syringes as fast as possible.

TABLE 1

Optiray 320
4 French Catheter

| Operator | Control (8 mL) | Syringe 10/120 (7.5 mL) | Control (10 mL) | Syringe 10/120 (10 mL) | Control (12 mL) | Syringe 10/120 (12.5 mL) | Control (25 mL) | Syringe 10/120 (25 mL) |
|---|---|---|---|---|---|---|---|---|
| User 1 | 1.434 | 2.235 | 1.221 | 1.997 | 1.327 | 1.324 | 0.673 | 0.786 |
| User 2 | 0.833 | 1.900 | 0.721 | 0.995 | 0.592 | 0.705 | 0.326 | 0.397 |
| User 3 | 0.577 | 1.496 | 0.584 | 1.048 | 0.547 | 0.832 | 0.281 | 0.465 |

TABLE 2

Optiray 320
6 French Catheter

| Operator | Control (8 mL) | Syringe 10/120 (7.5 mL) | Control (10 mL) | Syringe 10/120 (10 mL) | Control (12 mL) | Syringe 10/120 (12.5 mL) | Control (25 mL) | Syringe 10/120 (25 mL) |
|---|---|---|---|---|---|---|---|---|
| User 1 | 3.613 | 3.260 | 2.367 | 3.904 | 2.231 | 3.950 | 1.424 | 2.912 |
| User 2 | 1.756 | 3.401 | 2.141 | 2.141 | 1.211 | 1.756 | 0.597 | 1.451 |
| User 3 | 1.536 | 2.114 | 2.575 | 2.575 | 1.205 | 1.617 | 0.593 | 1.991 |

TABLE 3

Optiray 350
4 French Catheter

| Operator | Control (8 mL) | Syringe 10/120 (7.5 mL) | Control (10 mL) | Syringe 10/120 (10 mL) | Control (12 mL) | Syringe 10/120 (12.5 mL) | Control (25 mL) | Syringe 10/120 (25 mL) |
|---|---|---|---|---|---|---|---|---|
| User 1 | 1.398 | 1.695 | 1.041 | 0.989 | 1.108 | 0.857 | 0.455 | 0.401 |
| User 2 | 0.717 | 1.019 | 0.431 | 0.630 | 0.636 | 0.500 | 0.220 | 0.222 |
| User 3 | 0.279 | 1.151 | 0.428 | 0.612 | 0.391 | 0.501 | 0.214 | 0.481 |

TABLE 4

Optiray 350
6 French Catheter

| Operator | Control (8 mL) | Syringe 10/120 (7.5 mL) | Control (10 mL) | Syringe 10/120 (10 mL) | Control (12.5 mL) | Syringe 10/120 (12.5 mL) | Control (25 mL) | Syringe 10/120 (25 mL) |
|---|---|---|---|---|---|---|---|---|
| User 1 | 2.523 | 2.923 | 2.026 | 2.285 | 2.078 | 3.567 | 0.927 | 1.981 |
| User 2 | 1.428 | 2.525 | 0.993 | 1.362 | 1.575 | 1.348 | 0.476 | 1.269 |
| User 3 | 1.186 | 1.973 | 1.140 | 1.570 | 0.993 | 1.526 | 0.419 | 1.170 |

TABLE 5

Visipaque
4 French Catheter

| Operator | Control (8 mL) | Syringe 10/120 (7.5 mL) | Control (10 mL) | Syringe 10/120 (10 mL) | Control (12 mL) | Syringe 10/120 (12.5 mL) | Control (25 mL) | Syringe 10/120 (25 mL) |
|---|---|---|---|---|---|---|---|---|
| User 1 | 0.965 | 1.451 | 0.687 | 0.678 | 0.763 | 0.701 | 0.305 | 0.276 |
| User 2 | 0.458 | 0.721 | 0.411 | 0.497 | 0.465 | 0.412 | 0.149 | 0.215 |
| User 3 | 0.142 | 0.875 | 0.237 | 0.510 | 0.224 | 0.271 | 0.120 | 0.390 |

TABLE 6

Visipaque
6 French Catheter

| Operator | Control (8 mL) | Syringe 10/120 (7.5 mL) | Control (10 mL) | Syringe 10/120 (10 mL) | Control (12 mL) | Syringe 10/120 (12.5 mL) | Control (25 mL) | Syringe 10/120 (25 mL) |
|---|---|---|---|---|---|---|---|---|
| User 1 | 2.229 | 2.195 | 1.562 | 1.477 | 1.506 | 2.807 | 0.682 | 1.223 |
| User 2 | 1.147 | 1.764 | 0.768 | 0.967 | 1.299 | 1.061 | 0.250 | 0.929 |
| User 3 | 0.854 | 1.639 | 0.530 | 1.115 | 0.702 | 1.071 | 0.363 | 0.960 |

TABLE 7

Water
4 French Catheter

| Operator | Control (8 mL) | Syringe 10/120 (7.5 mL) | Control (10 mL) | Syringe 10/120 (10 mL) | Control (12 mL) | Syringe 10/120 (12.5 mL) | Control (25 mL) | Syringe 10/120 (25 mL) |
|---|---|---|---|---|---|---|---|---|
| User 1 | 3.755 | 4.684 | 2.621 | 5.262 | 3.578 | 3.591 | 1.935 | 3.140 |
| User 2 | 3.007 | 4.207 | 2.605 | 3.397 | 2.588 | 2.579 | 1.704 | 2.324 |
| User 3 | 2.783 | 3.496 | 2.579 | 3.885 | 2.777 | 3.232 | 1.816 | 2.422 |

TABLE 8

Water
6 French Catheter

| Operator | Control (8 mL) | Syringe 10/120 (7.5 mL) | Control (10 mL) | Syringe 10/120 (10 mL) | Control (12 mL) | Syringe 10/120 (12.5 mL) | Control (25 mL) | Syringe 10/120 (25 mL) |
|---|---|---|---|---|---|---|---|---|
| User 1 | 5.807 | 6.844 | 5.154 | 6.461 | 5.169 | 5.644 | 2.951 | 5.573 |
| User 2 | 4.379 | 5.618 | 4.026 | 4.207 | 4.109 | 4.364 | 2.254 | 3.818 |
| User 3 | 4.054 | 4.820 | 4.351 | 5.099 | 4.583 | 4.805 | 2.036 | 4.529 |

Figure 4:
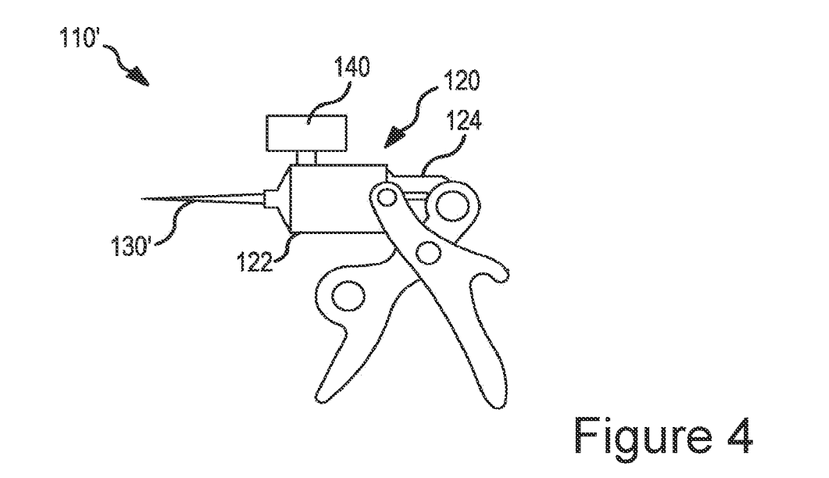
FIG. 4 is a schematic representation of a system including a hand-held syringe and a needle, with the syringe configured to be operated, for example, in discography procedures, with one hand.

Another embodiment of a fluid delivery system 110' is shown in FIG. 4, and which illustrates another application for syringes in accordance with syringes 10, 120. System 110' also includes a syringe 120 but, in place of or in addition to the catheter 130 of system 110 (FIG. 3A), system 110' includes a needle 130'.

When system 110' is to be used in procedures where it is useful or necessary to monitor pressure, a pressure gauge 140 of a suitable, known type (e.g., a manometer, etc.) may also be included. Pressure gauge 140 may be in fluid communication with an interior of a barrel 122 of syringe 120.

When system 110' is used in discography procedures, needle 130' may be connected directly to barrel 122, or it may be connected to barrel 122 by way of a catheter or other tubing. The size of needle 130' may be less than 16 gauge in size. As an example, when a 20 gauge needle (i.e., having an outer diameter of about 0.036 inch ((about 0.9 mm) and an inner diameter of about 0.025 inch (about 0.6 mm)) with a length of at least about 5 cm is employed, a relatively small 16 gauge needle (i.e., having an outer diameter of about 0.065 inch (about 1.7 mm) and an inner diameter of about 0.047 inch (about 1.2 mm)) or 17 gauge needle (i.e., having an outer diameter of about 0.058 inch (about 1.5 mm) and an inner diameter of about 0.042 inch (about 1.1 mm)) may be used as the guide needle. When needles that are smaller than 20 gauge in size are used, guide needles that are smaller than 16 gauge may likewise be used.

In the discography process, syringe 120 that includes a barrel 122 with a volume of as small as about 5 ml may be operated with a single hand of a user, including introducing the desired amount of pressure into the intervertebral disk, holding the pressure, and releasing the pressure. Since only one hand is required, the other hand is freed for other purposes, such as holding the needle, catheter, or tubing in place, stabilizing the subject, or the like.

Figure 5:
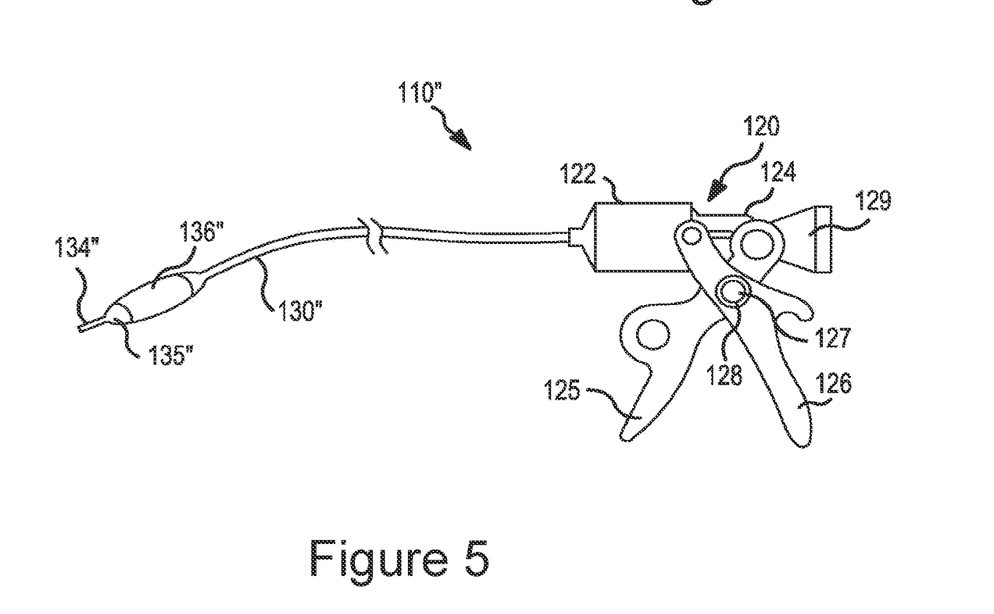
FIG. 5 is a schematic representation of a system that includes a hand-held, hand-operated syringe and an angioplasty catheter, which may be used in angioplasty procedures.

Turning now to FIG. 5, an embodiment of a system 110" in which a proximal end 132" of an angioplasty catheter 130" is coupled to a barrel 122 of syringe 120. A pressure gauge (e.g., FIG. 4) may be associated with syringe 120, for example, in fluid communication with an interior of barrel 122 of syringe 120. A distal end 134" of angioplasty catheter 130" is configured for insertion into a blood vessel of the body of a subject. Distal end 134" includes a balloon 135", and may include a stent 136" on balloon 135".

In an example of the use of system 110", syringe 120 may be used to inflate balloon 135". Specifically, bottom ends of handles 125, 126 (i.e., the portions of handles 125 and 126 that are located beneath a pivot point 127) are forced together, forcing a plunger 124 of syringe 120 into barrel 122. As plunger 124 moves further into barrel 122, fluid (e.g., air) within barrel 122 is displaced into catheter 130" and, eventually, to balloon 135".

It has only recently been determined that a syringe 120 having a barrel 122 with a displacement volume of about 7 ml may be operated with one hand to generate and hold as much as about 20-24 atmospheres (atm.) of pressure within balloon 135" without the requirement of locks or microadjustment mechanisms. A 12.5 ml barrel 122 may be used with syringe 120 to generate and hold as much as about eight atmospheres to about 12 atm. of pressure within balloon 135".

When locks or microadjustment mechanisms are associated with the handles 125, 126 of the syringe 120, even more pressure may be generated and held. For example, using a syringe 120 that includes locks and microadjustment features (see, e.g., U.S. Provisional Patent Application 60/853,878) and that includes a barrel 122 with a volume of 12.5 ml, up to about 30 atm. of pressure may be generated within an angioplasty balloon 135". Similarly, it has been discovered that a syringe 120 with a barrel displacement volume of about 25 ml may be used to generate as much as about four atm. to about six atm. in balloon 135" with one hand, and up to about 30 atm. of pressure within balloon 135" when locks or microadjustment mechanisms are associated with the handles 125, 126 of the syringe 120. When barrel 122 of syringe 120 has a displacement volume of about 50 ml, it may be used to generate as much as about two atm. to about three atm. of pressure within balloon 135" when one hand is used to operate syringe 120, and up to about 15 atm. of pressure when locks or microadjustment mechanisms are associated with the handles 125, 126 of the syringe 120.

A method of using a hand-held, hand-operated syringe of the type described in U.S. Provisional Patent Application 60/853,878 (fitted with a suitable pressure gauge of known configuration) in an angioplasty procedure includes inflation of balloon 135" to nominal pressure by operating syringe 120, via handles 125 and 126, with one hand. The user's other hand may be used to hold catheter 130" in place (and to prevent removal of catheter 130" from the body of a subject during the inflation process). Once nominal pressure has been obtained, the same hand that has been used to move handles 125 and 126 may be used to operate a locking element 128 that retains a desired location between handles 125 and 126. Additionally, that same hand may be used to operate a microadjustment mechanism 129 associated with handles 125 and 126 to finely adjust the relative positions of handles 125 and 126, as well as the position of plunger 124 within barrel 122, and, thus, further increase or decrease (by small amounts) pressure within balloon 135" (which pressure may be visually displayed by pressure gauge 140 (FIG. 4)), if necessary. By releasing locking element 128 (e.g., with the same hand that grasps handles 125 and 126) and allowing the bottom ends of handles 125 and 126 to separate from one another as the resilience of balloon 135" and of the vessel within which balloon 135" (and, possibly, of surrounding tissues) is disposed forces fluid out of balloon 135", proximally through catheter 130", and back into barrel 122 of syringe 120.

In other embodiments, a system that includes syringe 120 may be used for a variety of other purposes (e.g., injection of orthopedic glue, hemodynamic monitoring (e.g., invasive cardiac output measurement), injection or aspiration of viscous substances through elements, such as catheters, needles, or the like, with inner diameters of 0.052 inch or smaller, etc.) in place of more expensive apparatus.

The simple design and manufacture of syringe 120 makes it much less expensive than conventional angioplasty inflators, power syringes, discography syringes, and similar devices. It may, therefore, be considered to be a disposable (single-procedure use) device, which eliminates the need for sterilization and reduces contamination issues that may be presented due to incomplete or ineffective sterilization. Costs may be further reduced in embodiments where handles 125 and 126 are configured to be reused with different, disposable syringe barrels 122, plungers 124, and plunger tips, which may be configured as single-use cartridges that are configured for quick assembly with and disassembly from handles 125 and 126. In embodiments where handles 125 and 126 are reused, less waste is created.

Although the foregoing description contains many specifics, these should not be construed as limiting the scope of the present invention, but merely as providing illustrations of some exemplary embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed:

1. A hand-held angiography system comprising:
   a catheter including a proximal end, a distal end, and an outer diameter of less than 6 French;
   contrast media; and
   a hand-held, hand-operated syringe, including:
      a syringe barrel that couples to the proximal end of the catheter;
      a plunger within the syringe barrel and movable along a length of the syringe barrel; and
      a handle including:
         a first member including a gripping end, an intermediate portion, and a plunger attachment end pivotally coupled to the plunger;
         a second member including a gripping end, an intermediate portion, and a barrel attachment end pivotally coupled to the syringe barrel; and
         a hinge pivotally coupling the intermediate portion of the first member and the intermediate portion of the second member,
         the first member, the second member, and the hinge having a crossing pivotal arrangement that provides a mechanical advantage that enables the hand-held, hand-operated syringe to force the contrast media into and through the catheter at a substantially constant rate of at least 0.5 mL/s that optimizes a density of contrast-enhanced images while an individual operates the handle with one hand without further assistance.

2. The hand-held angiography system of claim 1, wherein the syringe barrel comprises a cylindrically shaped recess defined therein and sized to couple to the proximal end of the catheter.

3. The hand-held angiography system of claim 1, wherein the hand-held, hand-operated syringe is capable of forcing the contrast media through the catheter at a rate equal to or greater than about 0.5 mL/second.

4. The hand-held angiography system of claim 1, wherein the hand-held, hand-operated syringe is capable of forcing the contrast media through the catheter at a rate equal to or greater than about 1.0 mL/second.

5. The hand-held angiography system of claim 1, wherein the hand-held, hand-operated syringe is capable of forcing the contrast media through the catheter at a rate equal to or greater than about 2.0 mL/second.

6. The hand-held angiography system of claim 1, wherein the hand-held, hand-operated syringe is capable of forcing the contrast media through the catheter at a rate equal to or greater than about 3.0 mL/second.

7. The hand-held angiography system of claim 1, wherein the hand-held, hand-operated syringe is capable of forcing the contrast media through the catheter at a rate equal to or greater than about 5.0 mL/second.

8. The hand-held angiography system of claim 1, wherein the outer diameter of the catheter is no more than 5 French.

9. The hand-held angiography system of claim 1, wherein the outer diameter of the catheter is no more than 4 French.

10. The hand-held angiography system of claim 1, wherein the catheter is of a length of at least about 65 cm.

11. The hand-held angiography system of claim 1, wherein the hand-held, hand-operated syringe comprises an injection syringe, with the gripping end of the first member capable of being manipulated by at least one finger of an individual's hand and the gripping end of the second member capable of being held in place by a thumb or a palm of the user's hand.

12. The hand-held angiography system of claim 1, wherein the hand-held, hand-operated syringe comprises an aspiration syringe, with the gripping end of the first handle member capable of being held in place by a thumb or a palm of a user's hand and the gripping end of the second handle member capable of being manipulated by at least one finger of the individual's hand.

13. The hand-held angiography system of claim 1, wherein a length of the first member of the handle of the hand-held, hand-operated syringe is greater than a length of the second member of the handle of the hand-held, hand-operated syringe.

14. A hand-held catheter system comprising:
   a balloon catheter including a distal end for insertion into a body of a subject, a balloon adjacent to the distal end, and a proximal end, the balloon catheter having an outer diameter of less than 6 French;
   a hand-held, hand-operated syringe, including:
      a syringe barrel that couples to the proximal end of the balloon catheter;
      a plunger within the syringe barrel and movable along a length of the syringe barrel; and
      a handle including:
         a first member including a gripping end, an intermediate portion, and a plunger attachment end pivotally coupled to the plunger;
         a second member including a gripping end, an intermediate portion, and a barrel attachment end pivotally coupled to the syringe barrel; and a hinge pivotally coupling the intermediate portion of the first member and the intermediate portion of the second member, the first member, the second member, and the hinge having a crossing pivotal arrangement that provides a mechanical advantage sufficient to inflate the balloon of the balloon catheter at a substantially constant rate while an individual operates the handle with one hand without further assistance.

15. The hand-held catheter system of claim 14, wherein the balloon catheter comprises an angioplasty balloon catheter.

16. The hand-held catheter system of claim 14, further comprising:

a stent carried by the balloon of the balloon catheter.

17. The hand-held catheter system of claim 14, wherein the balloon catheter has an outer diameter of 5 French or less.

18. The hand-held catheter system of claim 17, wherein the balloon catheter is a 4 French balloon catheter.

19. The hand-held catheter system of claim 14, wherein a length of the first member of the handle of the hand-held, hand-operated syringe is greater than a length of the second member of the handle of the hand-held, hand-operated syringe.

* * * * *